United States Patent
Bell

(10) Patent No.: US 6,234,980 B1
(45) Date of Patent: May 22, 2001

(54) NEEDLESTICK FIRST RESPONSE KIT AND METHOD OF USING SAME

(75) Inventor: Craig J. Bell, E. Swanzey, NH (US)

(73) Assignee: MedCare Medical Group, Inc., E. Swanzey, NH (US)

( * ) Notice: Subject to any disclaimer, the term of this patent is extended or adjusted under 35 U.S.C. 154(b) by 0 days.

(21) Appl. No.: 09/384,528

(22) Filed: Aug. 27, 1999

(51) Int. Cl.⁷ .................................................. A61B 5/00
(52) U.S. Cl. ....................... 600/578; 604/314; 604/316; 606/203
(58) Field of Search ........................ 600/578; 604/314, 604/316; 606/203

(56) References Cited

U.S. PATENT DOCUMENTS

| | | | | |
|---|---|---|---|---|
| 35,038 | * | 4/1862 | Pierce | 606/203 |
| 4,287,819 | | 9/1981 | Emerit | 99/472 |
| 5,241,969 | * | 9/1993 | Carson et al. | 600/566 |
| 5,800,781 | * | 9/1998 | Gavin et al. | 600/576 |
| 5,857,983 | * | 1/1998 | Douglas et al. | 600/583 |
| 5,947,957 | * | 9/1999 | Morris | 606/13 |
| 5,984,876 | * | 11/1999 | Emerit | 600/578 |
| 6,015,392 | * | 1/1999 | Douglas et al. | 600/583 |
| 6,071,249 | * | 6/2000 | Cunningham et al. | 600/578 |
| 6,120,464 | * | 9/2000 | Racchini et al. | 600/573 |

* cited by examiner

*Primary Examiner*—Gary Jackson
(74) *Attorney, Agent, or Firm*—Davis & Bujold, P.L.L.C.

(57) ABSTRACT

A method and apparatus for treatment of inadvertent sharps/needlestick injuries to healthcare workers and the like. The method and apparatus provide a tourniquet for restricting blood flow to the site of the sharps injury, an apparatus for mechanically applying a negative pressure directly to the site of the sharps injury and removing bodily fluids and blood therefrom, a mechanism for delivering an antimicrobial/antiviral agent(s) to the site, and bandage for covering the site of the sharps injury following treatment. The first aid components are preferable all contained within a convenient time saving kit to facilitate ease of use by an injured individual.

20 Claims, 5 Drawing Sheets

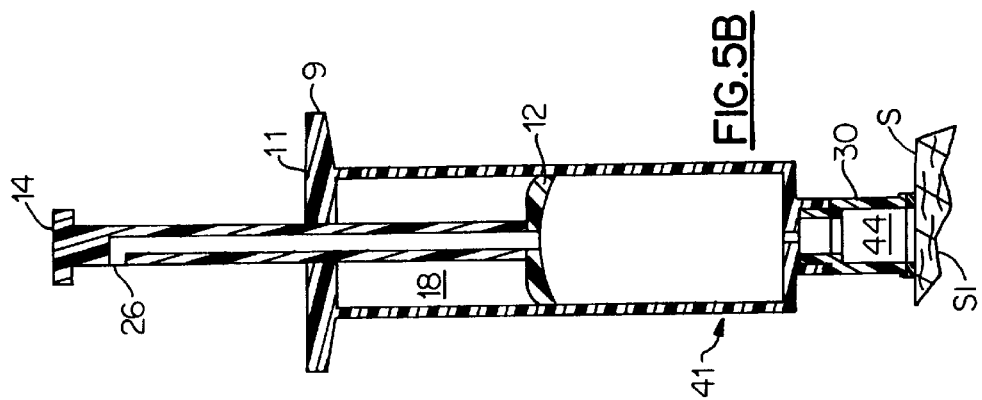
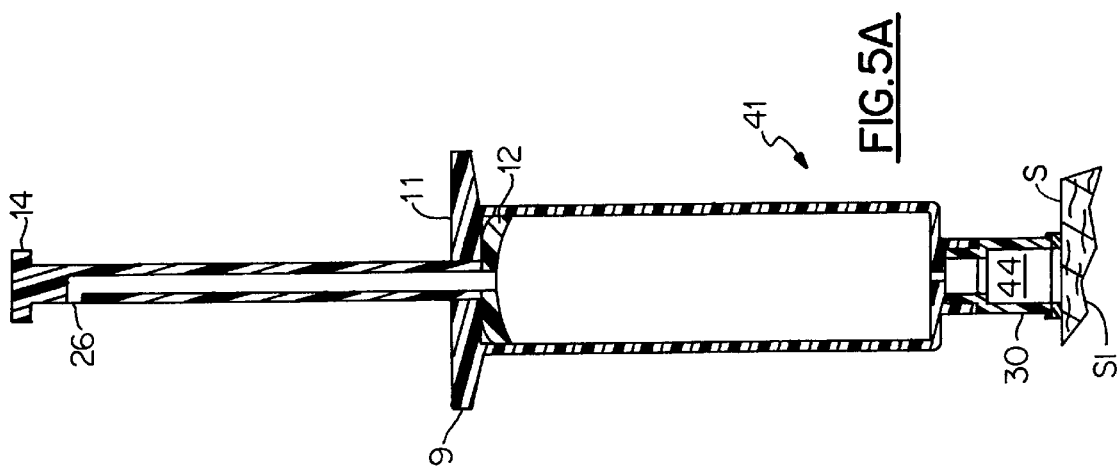
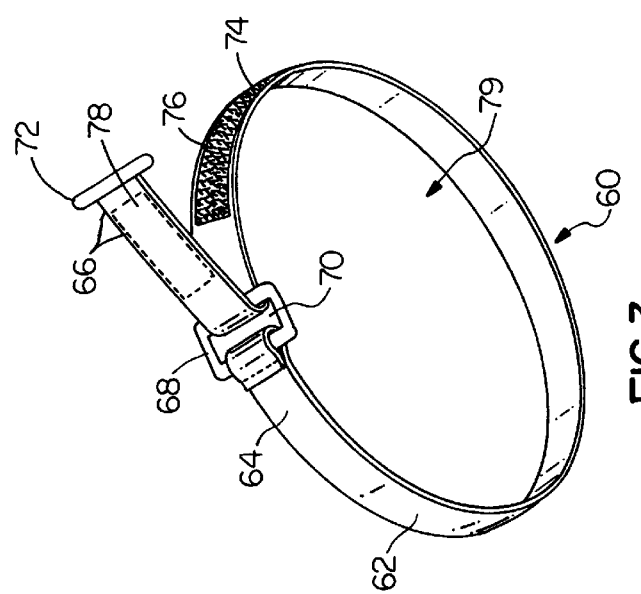

NEEDLESTICK FIRST RESPONSE KIT AND METHOD OF USING SAME

The present invention relates generally to an improved treatment for inadvertent sharps/needlestick injuries to healthcare workers and the like, and, more particularly, to an apparatus for restricting blood flow to the area of the sharps injury, an apparatus for mechanically applying a sub-atmospheric pressure directly to the site of the sharps injury, a mechanism for delivering an antimicrobial/antiviral agent (s) to the site, and a convenient time saving kit for containing all of these components.

BACKGROUND OF THE INVENTION

There are approximately 1 million sharps and/or needlestick related injuries reported in the United States annually. This equates to about two needlestick injuries every minute. However, it is also reported that about 50% of the injuries that occur go unreported. Taking the unreported injuries into consideration, there could be upwards of 2 million sharps and/or needlestick injuries per year in this country.

Sharps related injuries carry the potential of infecting the injured person with a host of diseases which include, for example, human immunodeficiency virus (HIV), hepatitis B virus (HBV), and hepatitis C virus (HCV). According to a 1997 report from the Centers for Disease Control and Prevention, the risk of HIV seroconversion, after a needlestick or cut exposure to HIV-infected blood is 0.3%. This risk increases with: 1) an increase in the quantity of infected blood being introduced into the injured tissue, 2) a higher viral load in the source of the contaminated blood at the time of the exposure, 3) an increased depth of the wound, and 4) if no post exposure treatment was administered.

Hollow bore needles, for example, increase the risk of contracting a disease, due to a sharps and/or needlestick related injury, because such needles can both deliver relatively large amounts of infected blood and achieve a fairly deep percutaneous penetration. It is to be appreciated that patients who are in the laterstages of AIDS usually have a high HIV load in their blood. They also require significant medical treatment including vascular access via hollow bore needles. Some of these patients get dementia and become relatively uncooperative during the later stages of AIDS prior to death. This condition can further increase the potential risk of an inadvertent needlestick injury to a healthcare worker.

As of December 1996, the Centers for Disease Control and Prevention had reported 52 documented cases and 111 possible cases of occupationally acquired HIV among healthcare workers in this country. A majority of these cases, i.e. 87%, are directly related to a sharps injury.

While HIV is a serious concern, hepatitis has a higher transmission rate and can be just as deadly. Although HBV carries a risk of infection of about 30%, which is one hundred times greater than HIV, healthcare workers can and should get vaccinated against this disease. HCV is a different story because of the lack of an available vaccine. HCV carries a about 10% risk of infection. Almost everyone contracting HCV will become a chronic carrier and about two-thirds will go on to have elevated liver enzymes requiring expensive drug treatment. HCV is currently the leading cause for liver transplant which costs upward of $500,000.

Currently on the market, there are numerous devices that shield, contain, and/or facilitate removal of a needle to minimize the risk of a healthcare worker getting stuck, and possibly infected, by a contaminated sharps needle. Such prior art devices, however, have only penetrated about 15% of the total United States market. The reason for this is several fold: such devices increase the cost of using the needle, some devices may be somewhat more difficult to utilize, and healthcare worker indifference to the seriousness of the potential problem. The bottom line is that needlesticks are occurring at a rate of about 2 to 4 per minute each day.

State legislation, starting with the state of California, is putting teeth into current OSHA regulations. These new regulations are requiring the use of sharps protection devices. The use of such devices has been shown to reduce the incidence of injury by up to 85%. But such efforts have not completely eliminated all of the sharps injuries.

The current procedure for post needlestick injury is to immediately administer first aid. This is generally defined as expressing blood from the site of the sharps injury in an attempt to flush the wound with one's own blood as completely as possible. If the expressing procedure is successfully executed, this can substantially reduce the viral loading at the site and hence substantially reduce the chance of infection resulting from the needle stick. Following the expressing step, it is next suggested to wash the injured area with an antimicrobial soap. There are some data that indicate vigorously scrubbing of injured area with an antimicrobial/antiviral agent(s) is beneficial. Next, the healthcare employee needs to report the incident to the appropriate authorities and be examined by a physician. Finally, once all of the above steps are completed and a full medical assessment is made, a treatment program can then be developed for the injured individual. It is to be appreciated that the resulting treatment program possibly involves a multi-drug regiment to reduce the risk of infection.

It is to be appreciated that the fact that a needlestick injury has occurred is very stressful to the injured individual. As a result of this, self-administering first aid by the individual stuck with the needle, during this stressful time, may possibly not be properly or completely administered. Anything, procedure or system, that can minimize or eliminate the guess work out of the initial first aid treatment because of a needlestick injury can insure more consistent and effective handling of such sharps injuries.

SUMMARY OF THE INVENTION

Wherefore, it is an object of the present invention to overcome the aforementioned problems and drawbacks associated with the prior art methods.

In particular, the present invention relates to a system for initial treatment of a sharps or needlestick injury via the application of a sub-atmospheric pressure to the site of the sharps injury. The present invention provides a single patient a disposable and economical kit to provide swift, efficient, and effective needlestick injury first aid as well as the method of performing such first aid. In its most basic form, the invention is a mechanical device for generating negative pressure at the site of a wound. In a broader form of the invention, it is a medical kit for the initial treatment of a sharps needlestick injury that contains a mechanical device for generating negative pressure, a tourniquet for slowing the flow of blood of the injured individual to and from the site of the sharps injury, at least one antimicrobial/antiviral agent(s) for washing and/or scrubbing the wound, and at least one bandage(s) for covering the wound following initial treatment.

In a preferred embodiment of the invention, the device for mechanical generation and maintenance of sub-atmospheric pressure is achieved by a manual arrangement, not relying on an auxiliary power, utilizing a one-handed technique.

According to another embodiment, the mechanical generation of the sub-atmospheric pressure is achieved by using a conventional syringe with a thumb ring for activating the plunger or piston, so that the plunger or piston can be operated via movement of a single hand of a user. This motion generates a negative pressure at the tip of the syringe.

Other embodiments include the use of vacuum tubes typically used for sampling venous blood, portable and hospital line vacuum pumps, and suction cups.

A primary object of the present invention is to provide a procedural kit that contains all of the necessary components to administer swift initial treatment to a site of a sharps injury. This kit includes, but is not limited to the following; a tourniquet, a mechanical device (e.g. a syringe) for generating sub-atmospheric pressure, a surface interface between the injury and the mechanical device for generating the sub-atmospheric pressure, at least one antimicrobial/antiviral(s) substance, and at least one adhesive bandage(s).

Another object of the invention is to provide an intermediate chamber, between the surface interface and the vacuum source, to facilitate collecting blood and other bodily fluids that are withdrawn from the site of the sharps injured. This intermediate chamber will minimize splash and can be sealed and used as a mechanism for transporting the sample to a suitable laboratory for testing. If desired, this intermediate chamber may contain an absorbent material to collect and retain any extracted blood, bodily fluids, etc. The absorbent material may be impregnated with an antimicrobial/antiseptic(s) agent.

A further object of the invention is to provide an intermediate chamber that can readily seal around a circumference of a finger or thumb, for example, to deliver the generated sub-atmospheric pressure to the fingernail region of a stuck individual, which is not accessible/sealable with a flat surface sealing chamber.

A still further object of the invention is to provide a tourniquet which is designed to be easily placed on the arm, leg, limb, etc. and tightened using only one hand. This arrangement saves time by not having to find another person, if one is even available, to assist the injured individual and by quickly restricting the blood flow to the injured area without increasing the blood flow due to the injured individual running around in search of assistance.

Yet another object of the invention is a method of providing first response treatment to a sharps/needlestick injury by applying a tourniquet to reduce the blood flow to the area of the wound, applying a mechanically generated negative pressure to withdraw or extract blood and/or other bodily fluids from the wound, and then applying an antimicrobial/antiviral agent to the wound.

The focus of the present invention is the improvement over the first aid that is currently administered to an individual for needlestick injuries. The first improvement is to utilize a tourniquet around the injured area to reduce the perfusion to the area of the injury. Next, an improved process for expressing blood is administered to the needlestick or sharps injury. The present invention is directed at providing a more thorough blood expressing procedure to further minimize the possibility of contracting a disease from the sharps injury. In particular, the current practice of manually expressing blood from the injury site may well be forcing the contaminated blood, currently located within the wound, deeper into the tissue instead of forcing the contaminated blood out of the wound or puncture. The application of negative pressure, by a mechanical apparatus, achieves the desired blood and/or bodily fluid expression from the wound without the potential of driving the contaminated blood deeper into the tissue. In addition, the mechanical apparatus for expressing the blood and/or other bodily fluids from the wound also enables a greater drawing power or suction force than can normally be achieved by manually expressing with one's fingers. Lastly, the introduction of an antimicrobial/antiviral agent(s), to the site of the sharps injury, is preferably done just as the negative pressure is slowly released for the site of the sharps injury.

According to the present invention, the first step is to slow the flow of blood to the wound by apply a tourniquet. The second step is to express blood and/or other bodily fluids from the wound by applying a mechanically generated negative pressure directly to the site. The third step is to apply an antimicrobial/antiviral agent(s) to the site of the sharps injury, immediately following the expressing step. The fourth and final step is to apply an adhesive bandage to completely cover the site of the sharps injury.

The above and other objects of the present invention will become apparent to those skilled in the art to which this invention pertains and after a study of the present disclosure of the invention.

BRIEF DESCRIPTION OF THE DRAWINGS

The invention will now be described, byway of example, with reference to the accompanying drawings in which:

FIG. 3 is a diagrammatic perspective view of a unique tourniquet, according to the present invention;

FIG. 5A is a diagrammatic transverse cross sectional view showing use of the syringe assembly, in its initial retracted position, prior to expressing blood from a sharps' puncture site;

FIG. 5B is a diagrammatic transverse cross sectional view showing use of the syringe assembly, in its intermediate position, immediately prior to expressing blood from the sharps' puncture site;

DESCRIPTION OF THE PREFERRED EMBODIMENT(S)

Briefly described, the present invention relates to the swift, consistent, and efficacious kit and method for treatment of a sharps/needlestick injury. The kit and the method for treating a sharps injury, according to the present invention, are directed at reducing the potential of an infection resulting from a sharps injury.

The present invention, in its simplest form, is the application of sub atmospheric pressure to the site of a sharps/needlestick injury. The science behind an expressing procedure is that sub-atmospheric pressure withdraws blood and/or other bodily fluids from the percutaneous injury, flushing possible microbiological contamination from the sharps' puncture site. If the expressing procedure is successfully preformed, this reduces the amount of contamination remaining within the tissue and this, in turn, can substantially reduce the rate of seroconversion.

The following description is of a first embodiment of the present invention and is in no way meant to limit the scope of the syringe assembly. It is to be appreciated that there may be variations in the shape or size of the syringe, in its ability to be either manually or automatically operated, or in the materials used in the construction and in the orientation of the components.

Figure 1:
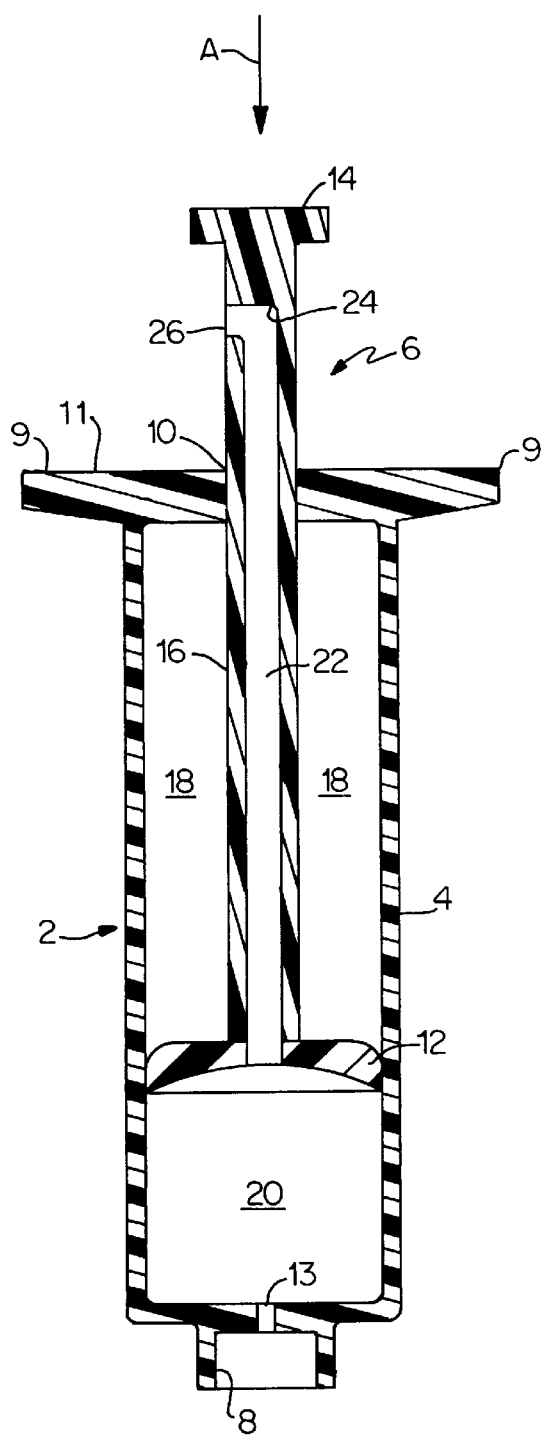
FIG. 1 is a cross-section side view of the syringe for use with the present invention.

Turning now to FIG. 1, a detail description concerning the source of negative pressure, e.g. a syringe 2, will now be provided. The syringe 2 has a generally cylindrical central barrel or body 4 which accommodates a piston rod unit 6 which is movable relative to the body 4. The body 4 is a generally hollow tubular member which has a smaller diameter orifice 8 at an open end thereof, the purpose of which will be described in further detail hereinafter, and is substantially closed at the opposite base end except for a small opening 10 in the base wall 11 which allows a portion of the piston-rod unit 6 to extend therethrough. The base wall has a pair of outwardly extending ears 9 integrally formed therewith.

The piston-rod unit 6 comprises a piston 12 which is interconnected with an actuating knob 14 by an elongate actuating rod 16. The piston 12 divides an interior of the body into a first chamber 18, located between the piston 12 and the closed base wall 11 of the body, and a second chamber 20, located between the piston 12 and the opened orifice end of the body. The piston 12 is designed to slide, in a sealing manner, relative to an inwardly facing surface of the cylindrical body 4 to generate desired air movement within the syringe 2. To assist with the desired air circulation, an axial passageway 22 is formed within and extends along a substantial length of the actuating rod 14. A first end of the axial passageway 22 communicates with the second chamber 20, via a central opening in the piston 12, while a second end of the passageway 22 terminates at an elbow 24 which communicates with an exhaust vent 26. Due to this arrangement, movement of the piston 12, relative to the body 4, normally expels air contained within the second chamber 20, if the orifice is closed, along the passageway 22 and out through the vent 26, while simultaneously generating a negative pressure within the first chamber 18, the purpose of which will be discussed below. If the orifice is not closed, air can be dispensed form the second chamber 20 out through the orifice 8, via a duct 13 establishing communication therebetween.

With the piston 12 in a retracted upper position adjacent base wall 11, the syringe 2 is held in one hand, in a conventional manner, with two fingers grasping around the ears 9 and a thumb, or the palm of the hand of the user, is positioned on the knob 14. As the knob 14 is moved in a direction of arrow A toward the body 4, such motion causes the piston 12 to slide axially along the inwardly facing cylindrical surface of the body 4 toward the opened end of the body 4. The air contained within the second chamber 20, between the piston 12 and the opened end of the body 4, during use, normally escapes to the surrounding environment by flowing along the passageway 22 and out through the vent 26. Such movement of the piston 12 along the inner surface of the cylindrical body also, in turn, creates a vacuum within the first chamber 18 as no air is allowed to enter the first chamber 18.

The vacuum or negative pressure in the first chamber 18 continues to increase until the piston 12 almost reaches its end travel position in which the piston 12 is located closely adjacent but spaced slightly from the opened end, e.g. the piston is spaced about 114 inches or so from an end wall supporting the duct 13. Once this occurs, the vent 26 initially becomes blocked by the base wall 11. As the piston 12 continues to move toward its end position, the vent 26 eventually establishes communication with the first chamber 18 and thus the negative pressure created within the first chamber 18 causes air, blood, bodily fluids, etc., to flow in through the orifice 8 and into the second chamber 20. The air, blood, bodily fluids, etc., then flow along the passageway 22 and into the first chamber 18 until the pressure in the first chamber 18 and the second chamber 20 become equalized with one another. Such relief of the negative pressure causes the desired expressing of blood from the site of the sharps injury and conveys all of the expressed blood, bodily fluids, etc. toward the second chamber 20, and the first chamber 18 via the passageway 22.

With reference now to FIG. 2, a preferred tip 30 for engagement with the orifice and use with the syringe 2 of FIG. 1 will now be described in detail. As can be seen in this Figure, the tip 30 comprises a rigid outer wall 32 which comprises a smaller diameter cylindrical section 34 which is connected to a larger diameter cylindrical section 36 via a smooth transition 38 located therebetween. The smaller diameter cylindrical section 34 is sized to have a slight interference fit with the orifice 8 of the syringe 2 so as to be captively retained therein. A through bore 40 extends completely through both the smaller and larger diameter cylindrical sections 34, 36 to facilitate communication between the sharps injury and the second chamber 20 of the syringe, via the orifice 8 and the duct 13, once attached to the syringe 2.

An outer periphery of an inlet 39 of the larger cylindrical section 36 is sized to completely encase or surround the site of the desired sharps injury, e.g the inlet outer periphery typically has a diameter of between ⅛ about 2 inches. It is to be appreciated that the size and shape of the outer periphery of the inlet for the larger cylindrical section 36 can vary from application to application. If desired, a perimeter sealing member 42, e.g. a rubber perimeter seal, can be adhesively secured or otherwise affixed to the outer periphery of the inlet 39 to enhance the ability of the tip 30 to seal against the outer layer of skin of the injured person. The sealing member 42 can be made from a closed cell foam, an elastomer polymer like silicone, and/or a pressure sensitive adhesive which is automatically exposed when the tip is removed from the kit-e.g. a release strip is adhered to a base of a tray and is peeled away from the tip upon removal, or the pressure sensitive adhesive is manually exposed only after the release strip is manually removed from the tip. The tip 30 defines an intermediate chamber 44 therein and the intermediate chamber 44 initially receives the blood and/or other fluids expressed or withdrawn from the site of the sharps injury SI by operation of the syringe 2.

The tip 30 is preferably manufactured from a polymeric material like polypropylene, polycarbonate, polyvinyl chloride or some other similar material that is able to maintain the sub-atmospheric pressure created during use of the syringe 2, according to the present invention, without collapsing.

Figure 2A:
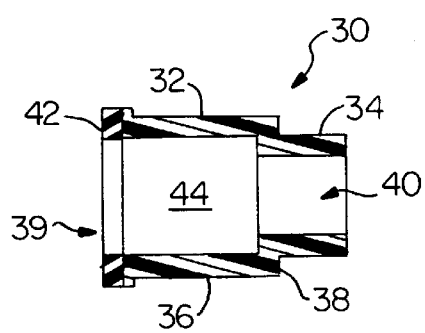
FIG. 2A is a diagrammatic transverse cross sectional view of an expressing tip with a sealing surface, according to the present invention.
Figure 2B:
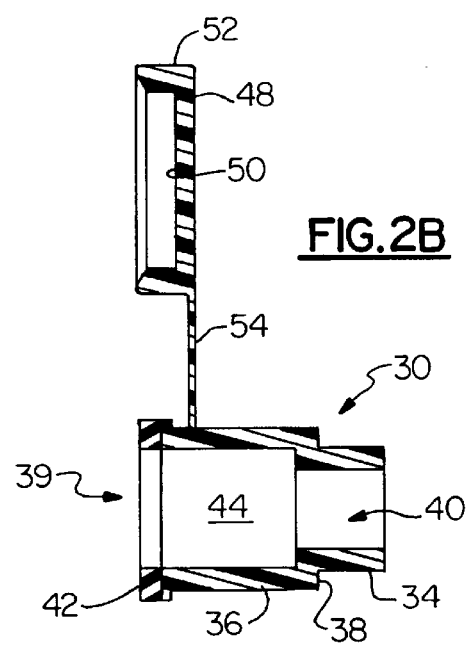
FIG. 2B is a diagrammatic transverse cross sectional view of a second embodiment of the expressing tip with both a sealing surface and a tethered closure cap, according to the present invention.

With reference to FIG. 2B, a second embodiment of the tip 30 is shown. This embodiment is very similar to the first embodiment except for the addition of a removable cap 48. The removable cap 48 has a flat planar base surface 50 and a cylindrical side wall 52 which is sized to have a locking interference fit with outer perimeter side wall of the inlet 39 of the larger cylindrical section 36. The cap 48 is connected to an intermediate area of the side wall 32 of the tip 30 by a flexible tether member 54 to prevent the cap 48 from being lost or misplaced. The tether member 54 is sufficiently long to allow the cap 48 to cover and seal the inlet 39 to the intermediate chamber 44 once a desired quantity of blood and/or bodily fluids are withdrawn by the syringe assembly according to the present invention.

Figure 2C:
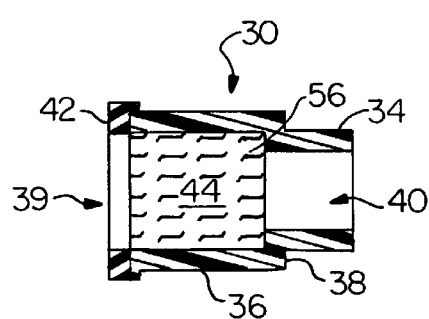
FIG. 2C is a diagrammatic transverse cross sectional view of a third embodiment of the expressing tip with a sealing surface and an absorbent material located within the intermediate chamber, according to the present invention.

FIG. 2C is a third embodiment of the tip 30 according to the present invention. This embodiment is very similar to the first embodiment except that an absorbent material 56 is located within the intermediate chamber 44 of at least the larger cylindrical section 36. The absorbent material 56 must be sufficiently porous to allow air and liquids to pass freely and readily therethrough so as to facilitate absorbing blood and/or other body fluids from the site of the sharps injury once such fluids are expressed from the site during use of the syringe 2. The absorbent material 56, located within the intermediate chamber 44, minimizes the possibility of any of the withdrawn blood and/or other bodily fluids from dripping, spilling or inadvertently discharging from inlet 39 of the tip 30 once the syringe assembly 41 is removed from the site of the sharps injury (the syringe 2 and the tip 30 are, in combination, referred to as the syringe assembly 41). If desired, the absorbent material 56 can be impregnated with an antimicrobial and/or a disinfecting agent(s) (not shown in detail).

Figure 2D:
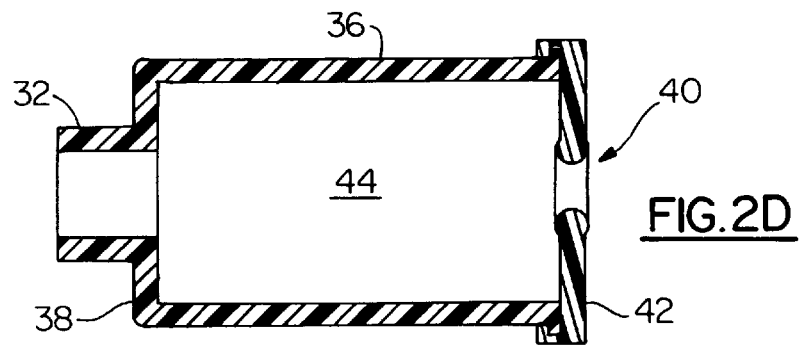
FIG. 2D is a diagrammatic transverse cross sectional view of a fourth embodiment of the expressing tip with a sealing wall for receiving a portion of a finger, according to the present invention.

FIG. 2D is a fourth embodiment of the tip 30 according to the present invention. This embodiment is very similar to the first embodiment except that the diameter of the larger diameter cylindrical section 36 is somewhat larger, than those of the previous embodiments, to at least partially receive an end portion of a finger or digit of a stuck individual at least partially within the intermediate chamber 44 via inlet 39. According to this embodiment, the sealing member 42 is still permanently supported by the periphery of the inlet 39 but is a planar member which extends radially inwardly to facilitate adequately sealing about the circumference of the finger, toe, or other limb or digit of the stuck individual. If desired, the inner circumference of the sealing member can be provided with an annular thickened area to facilitate insertion and removal of the finger, toe, or other limb with the tip 30. The inner circumference of the sealing member defines a passage which has a smaller dimension than the finger, toe, or other limb be received therein to achieve the desired seal therebetween. As with the previous embodiments, the sealing member enhances the ability of the tip 30 to properly seal against the outer layer of skin of the injured person while still allowing blood and/or other body fluids from the site of the sharps injury to pass freely and readily therethrough.

With reference to FIG. 3, an improved tourniquet 60, for use with the syringe assembly 41 according to the present invention, will now be described. As can be seen in this Figure, the tourniquet 60 comprises an elongate flexible member or strap 62 having a first end 64 and an opposed second end 66. The first end 64 of the tourniquet 60 is wrapped around a first section of a rigid buckle 68 and the first end 64 is attached, secured, stitched, etc., to itself to permanently secure the rigid buckle 68 to that end. The second end 66 passes through a central aperture 70 of the rigid buckle 68 and has a tab 72, or some other grasping member, permanently affixed thereto which allows the second end 66 to be easily grasped by a user while also preventing the tab 72 from passing back through central aperture 70 of the rigid buckle 68.

An intermediate portion of an outwardly facing surface 74 of the tourniquet 60 is provided with a first component of a touch fastener 76, e.g. a hook component, while the outwardly facing surface 74 of the second end 66 of the tourniquet 60 is provided with a second mating component of the touch fastener 78, e.g. a loop component. As shown in this Figure, the tourniquet 60 defines a central opening 79 for allowing an arm, leg, or other body extremity to readily pass therethrough.

When use of the tourniquet 60 is desired, the user retrieves the tourniquet 60 and places the tourniquet 60 around his or her arm, for example, by passing his or her arm through the central opening 79 of the tourniquet 60. Once this has occurred, the user grabs tab 72 and pulls the second end 66 of the tourniquet 60 away from the buckle 68 to exert a conventional constricting or tightening force on the tourniquet 60. Once the tourniquet 60 is sufficiently tightened, the user brings the second component of the touch fastener 78 into mating engagement with the first component of the touch fastener 76 to secure and maintain the tourniquet 60 in a securely tightened position.

Figure 4:
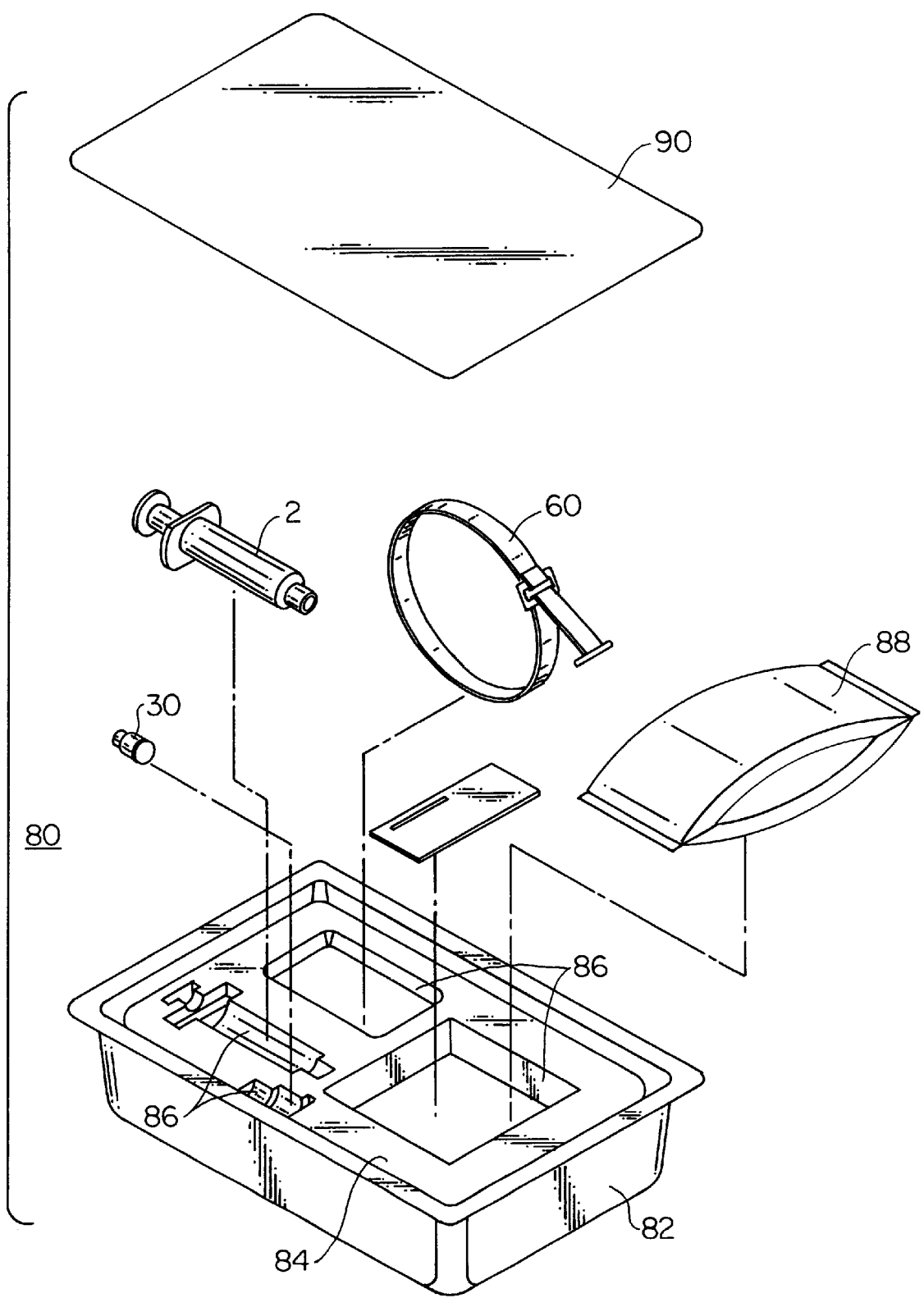
FIG. 4 is a diagrammatic perspective view of a complete needlestick first aid kit according to the present invention.

With reference to FIG. 4, a diagrammatic perspective view of a time saving and convenient needlestick first aid kit 80, according to the present invention, can be seen. The kit 80 comprises a base container 82 having an insert tray 84 with a plurality of cavities 86 formed therein. Each one of the cavities 86 is shaped or contoured to receive a desired component of the kit. For example, one cavity 86 is provided which is shaped and/or contour for receiving the syringe 2, at least one other cavity 86 is shaped and/or contoured to receive the tip 30, another cavity 86 is shaped and/or contoured to receive the tourniquet 60 and a final cavity 86 is shaped and/or sized to accommodate at least one conventional adhesive bandage or gauze 88, such as an antimicrobial/antiseptic gauze.

A conventional easily removable lid 90 is provided for sealingly retaining the various components within the base container 82. Preferably the lid 90 is transparent to allow easy viewing of all of the first aid components contained therein for periodic inspection of the kit.

The insert tray 84 can be manufactured from polystyrene or like materials and the lid can be manufactured form paper, Tyvek™, or some other plastic material. Once the kit is assembled with the necessary components, the sealed contents can be terminally sterilized by ethylene oxide or gamma radiation. It is contemplated that the kit contents can contain a small "clamshell" style enclosure. This can be thermally formed from polystyrene or polyvinyl chloride or injected molded from polyethylene.

Figure 5C:
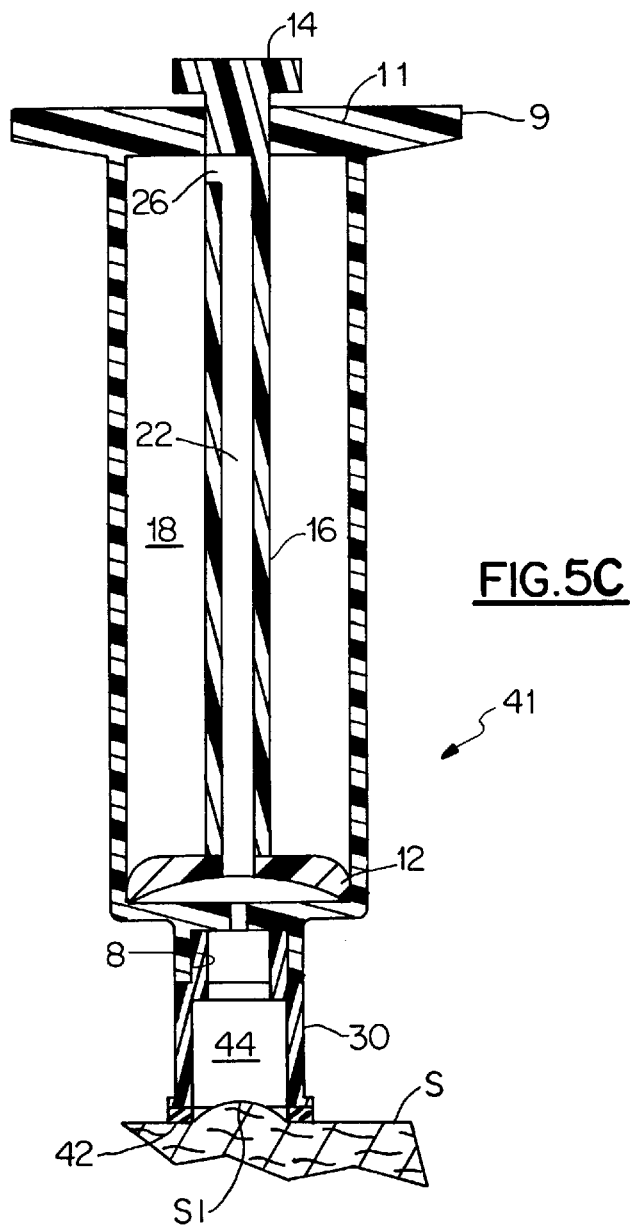
FIG. 5C is a diagrammatic transverse cross sectional view showing use of the syringe assembly in its collapsed final position which expresses blood and other bodily fluids from the sharps' puncture site.

When a sharps injury occurs, the user will first quickly retrieve the needlestick first aid kit 80 and remove the lid 90. Thereafter, the syringe 2 is removed and the smaller cylindrical section 34 of the tip 30 is engaged with the orifice 8 of the syringe 2. Next, the user removes the tourniquet 60 and passes his or her arm, leg, or other body part through the central opening 79 and appropriately tightens and secures the tourniquet 60 around the desired limb or other body part as described above. Once this has occurred, the user insures that the actuating knob 14 of the syringe 2 is in its fully retracted position, i.e. a position remote from a remainder of the syringe as shown in FIG. 5A. The user then positions the inlet 39 of the tip 30 over and around the site of the sharps injury SI so as to completely surround and encase the sharps injury SI with the sealing member 42. Thereafter, the user places his or her index and ring fingers each over one of the respective ears 9 and commences biasing the actuating knob 14, via his or her thumb or the palm of his or her hand, toward the ears 9 of the syringe 2 while still maintaining a sufficient and constant biasing pressure on the syringe 2 such that the sealing member 42 of the tip 30 is maintained in constant contact and engagement with the skin immediately adjacent the site of the sharps injury SI.

As the piston 12 moves within the body 4 of the syringe 2, the volume within the first chamber 18 increases which, in turn, creates a negative pressure within the first chamber 18. Such motion of the piston 12 simultaneously decreases the volume in the second chamber 20. As the volume in the second chamber 20 decreases, the displaced air flows axially along the passageway 22 and is exhausted out through the vent 26 as the contained air can only easily escape via this route since the flow path through the orifice 8 is blocked by the site of the sharps injury SI. Once the piston 12 has traveled substantially in its entire permissible travel distance, the negative pressure created within the first chamber 18 is substantially at a maximum negative pressure. Further downward movement of the piston 12 causes the vent 26 to communicate with the base wall 11, supporting the ears 9, and such communication temporarily blocks the vent 26 and prevents the exhaust of additional air, from the second chamber 20, out through the vent 26. Once the piston 12 is moved so that it is substantially clear of the base wall 11 of the syringe 2, the vent 26 then communicates with the first chamber 18 and the negative pressure, created within the first chamber 18, is instantaneously relieved by a sucking action generated along passageway 22. This sucking action, communicated via passageway 22, the second chamber 20 and the intermediate chamber 44, operates to withdraw or express blood, bodily fluids, etc., from the site of the sharps injury SI and to convey the withdrawn blood, bodily fluids, etc. through the inlet 39 of the tip 30 and into the intermediate chamber 44 and the second chamber 20. From there, some of the expressed blood, bodily fluids, etc. then flows along the passageway 22 and is conveyed to the first chamber 18.

It is important to note that the entire outer periphery of the inlet 39 of the tip 30, i.e. the entire periphery of the sealing member 42, must be constantly maintained in sealing engagement with the skin, surrounding the site of the sharps injury SI, to minimized the amount of any surrounding environment air which is inadvertently sucked into the first chamber 18. The maintaining of such a seal ensures that most of the generated negative pressure will be relieved solely by extracting or expressing blood and other bodily fluids from the sharps injury SI to maximize the expressing feature of the present invention.

Once this has occurred and the syringe has subjected the site of the sharps injury for a suitable period on time, e.g. between about 5 and about 180 second, the syringe 2 is slowly removed from the site of the sharps injury to relieve the generated negative pressure. If the tip 30 is provided with a cap 48, the cap 48 can then engage with the inlet 39 to seal the inlet 39 and prevent the inadvertent discharge of any of the expressed blood or other bodily fluids, etc., therefrom. Thereafter, the expressed and/or extracted blood and/or bodily fluids can be sent to an appropriate laboratory for necessary contamination testing to determine whether or not there was any contamination at all carried by the sharps or the needle causing the injury. The individual can then complete treatment of the sharps injury SI by washing and/or scrubbing the site of the sharps injury SI with an antimicrobial and/or an antiseptic and then applying an adhesive bandage to cover the site of the sharps injury SI. Finally, all of the various components of the kit can be reassembled and the kit 80 can then be returned to a desired facility for cleansing and/or refurbishing for subsequent reuse. More appropriately, the kit will be a single use, disposable kit.

Figure 6:
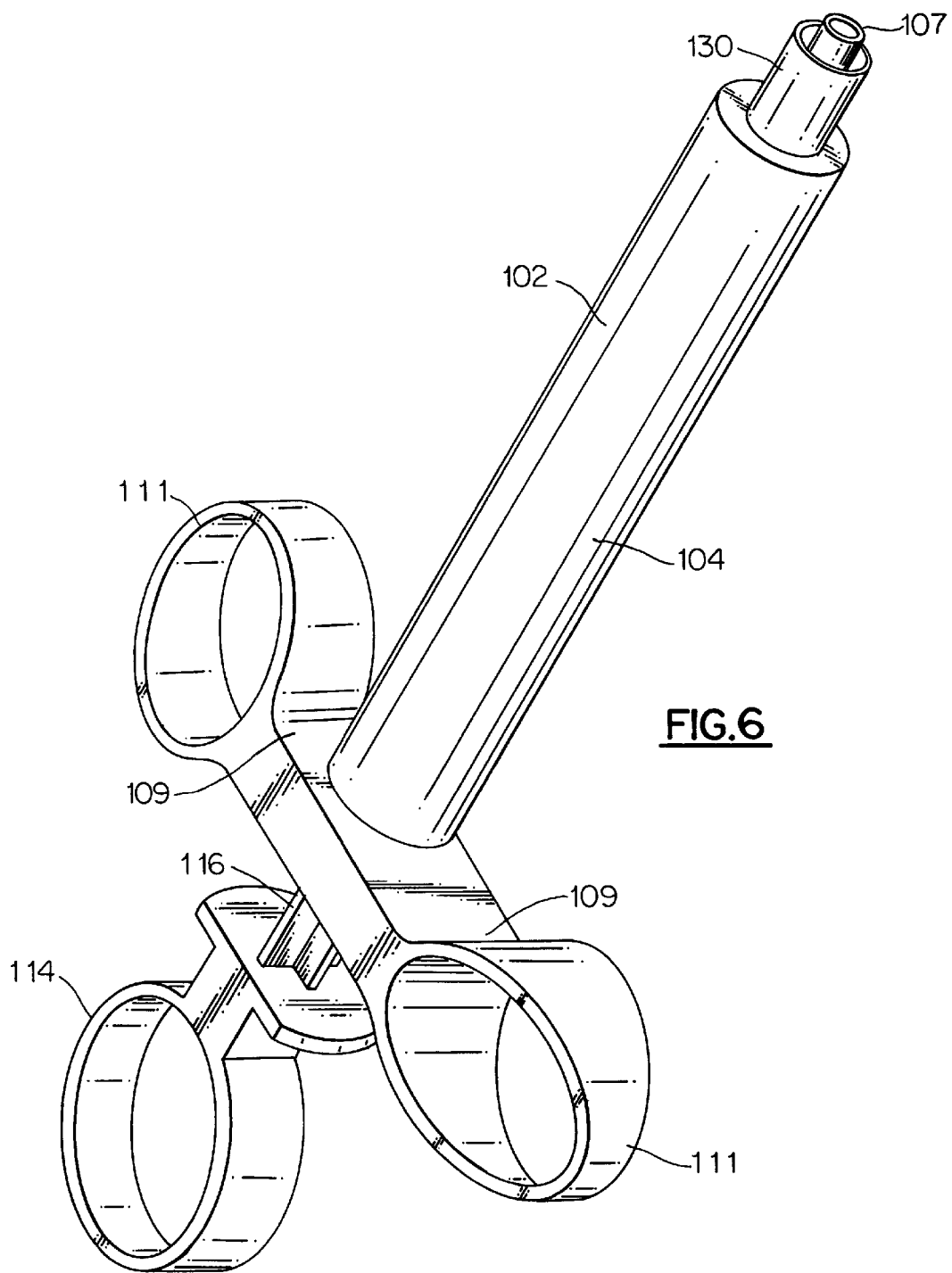
FIG. 6 is a diagrammatic perspective view of conventional syringe with thumb and finger rings.

With reference to FIG. 6, a perspective view of a second embodiment of the syringe 102, according to the present invention, can be seen. According to the embodiment, a standard style syringe 102, which is well known in the art, is employed. The syringe 102 comprises an exterior cylindrical barrel 104 having an inlet 107, at one end thereof, and a pair of opposed ears 109 located at the opposite end thereof. Each free end of the ears 109 supports a fixed finger ring 111. A piston or plunger (not shown) is accommodated within the barrel 104 and the plunger is fixedly connected to a movable finger ring 114 via an actuation rod 116. Movement of the plunger within the barrel 104, via operation of the movable finger ring 114 relative to the barrel 104, causes the plunger to move relative to the barrel 104 and create the desired vacuum in a conventional manner, i.e. the plunger is initially located, in this embodiment, adjacent the inlet 107 and move to a position adjacent end wall 113 to generate a negative pressure within the syringe 102. The tip 130, employed in this embodiment, is very similar to the tip shown in FIG. 2A, except that the tip 130 is either integral or permanently secured to orifice of the syringe 102 to save time when treating a sharps injury, i.e. it eliminates the need to attach the tip 130 to the syringe 102.

All types of needle sticks, sharps wounds, punctures, lacerations, etc. are referred to, in the above description and appended claims, as the site of the sharps injury. The terminology, "the site of the sharps injury", is intended to include any and all kinds of wounds, punctures, lacerations, injuries, etc. which are the caused by a sharp component, such as metal, glass, plastic, etc.

Since certain changes may be made in the above described apparatus and method, without departing from the spirit and scope of the invention herein involved, it is intended that all of the subject matter of the above description or shown in the accompanying drawings shall be interpreted merely as examples illustrating the inventive concept herein and shall not be constructed as limiting the invention.

Wherefore, I claim:

1. An apparatus for generating a negative pressure for expressing bodily fluid from a site of a sharp's injury, the apparatus comprising:

a substantially hollow body being closed at one end except for actuating rod aperture, and being open at the opposite end thereof, the open opposite end communicating with an orifice;

a piston being housed within the body, the piston being actuated by a knob located outside of the body, the knob being coupled to the piston via an actuating rod extending through the actuating rod aperture, the actuator rod having a passageway extending axially therealong, and one end of the passageway communicating with an end face of the piston facing the open end and an opposite end of the passageway communicating with an vent located adjacent the knob;

a hollow tip defining an intermediate chamber therein, the hollow tip having one end being coupled to the orifice, and the opposite end of the tip defining an inlet which is sufficiently large to encompass the site of the sharp's injury; and a perimeter portion of the inlet of the tip being provided with a flexible annular sealing member to facilitate sealing against skin adjacent the site of the sharp's injury and expressing bodily fluid from the site of the sharp's injury in and through the intermediate reservoir during utilization of the apparatus the inlet of the tip being sufficiently large to at least partially receive an end portion of a digit of an individual, and the flexible sealing member extends radially inwardly from a perimeter of the inlet to seal against a circumference of the end portion of the received digit.

2. The apparatus according to claim 1, wherein the tip is provided with a cap for closing the inlet of the tip, and the cap is connected to the tip by a flexible tether member.

3. The apparatus according to claim 1, wherein the tip has an absorbent material located within the intermediate chamber to facilitate absorbing and retaining of expressed bodily fluid[s] during use of the apparatus.

4. The apparatus according to claim 1, wherein the flexible sealing member has a passage with an inner circumference which has a diameter small than a diameter of the inlet to achieve a fluid tight seal with the received digit.

5. A kit of parts for providing first aid to needle stick injury, the kit of parts comprising a container housing the following first aid components:

a tourniquet comprising an elongate member having a first end and a second end, the first end of the tourniquet having a central aperture with the second end of the tourniquet extending through the central aperture, and the second end of the tourniquet having a mechanism for releasably fastening the second end of the tourniquet to the elongate member to secure the tourniquet in a tightened position; and a negative pressure apparatus having a tip for encasing the site of the sharp's injury and generating negative pressure in the tip to facilitate expressing bodily fluid from a site of a sharp's injury; the negative pressure apparatus comprising:

a substantially hollow body which being closed at one end except for actuating rod aperture, and being open at the opposite end thereof, the open opposite end communicating with an orifice;

a piston housed within the body, the piston being actuated by a knob located outside of the body, the knob being coupled to the piston via an actuating rod extending through the actuating rod aperture, the actuator rod having a passageway extending axially therealong, and one end of the passageway communicates with an end face of the piston facing the open end and an opposite end of the passageway communicates with an vent located adjacent the knob;

the tip defining an intermediate chamber therein, the tip has one end coupled to the orifice, and the opposite end of the tip defining an inlet which is sufficiently large to encompass the site of the sharp's injury; and a perimeter portion of the inlet of the tip is provided with a flexible annular sealing member to facilitate sealing against skin adjacent the site of the sharp's injury for facilitating expressing bodily fluid from the site of the sharp's injury in and through the intermediate reservoir during operation of the apparatus the inlet of the tip being sufficiently large to at least partially receive an end portion of a digit of an individual, and the flexible sealing member extends radially inwardly from a perimeter of the inlet to seal against a circumference of the end portion of the received digit.

6. The kit of parts according to claim 5, wherein the tip is provided with a cap for closing the inlet of the tip, and the cap is connected to the tip by a flexible tether member.

7. The kit of parts according to claim 5, wherein the tip has an absorbent material located within the intermediate chamber to facilitate absorbing and retaining of expressed bodily fluid during use of the apparatus.

8. The kit of parts according to claim 5, wherein the flexible sealing member has a passage with an inner circumference which has a diameter small than a diameter of the inlet to achieve a fluid tight seal with the received digit.

9. The kit of parts according to claim 5, wherein kit of parts includes a container with a plurality of cavities formed therein, and each of the cavities accommodates one of the first aid components of the kit of parts.

10. The kit of parts according to claim 5, wherein the container includes a lid for retaining all of the first aid components within the container when not in use.

11. The kit of parts according to claim 5, wherein the sealing member includes an adhesive and adhesive of the sealing member is covered by a release strip, at least one of the plurality of cavities is provided with an adhesive therein, and the adhesive is secured to the release strip so that the release strip is removed from the sealing member upon removing the tip from the container.

12. The kit of parts according to claim 5, wherein the piston divides an interior of the body into a first chamber, located between the piston and a closed base wall of the body, and a second chamber, located between the piston and the opened orifice end of the body.

13. The kit of parts according to claim 5, wherein the kit of parts further comprises:

a microbiological agent for cleaning of the site of the sharp's injury following expressing bodily fluid therefrom; and at lease one bandage for covering the site of the sharp's injury following cleaning.

14. A method of providing first aid to a site of a sharp's injury on a digit of an individual, the method comprising of steps:

placing a tourniquet about a limb of an individual having a needle stick and tightening the tourniquet to minimize the flow of blood in the limb of the individual with the needle stick;

encompassing a site of a sharp's injury with a negative pressure apparatus for generating negative pressure by passing the digit with the sharp's injury into an inlet of a tip of the negative pressure device and sealing a perimeter of the digit, with the sharp's injury, with a flexible perimeter sealing member of the tip, and the flexible perimeter sealing member having a passage with an inner circumference having a diameter small than a diameter of the inlet to achieve a fluid tight seal therebetween;

expressing bodily fluid from the site of the sharp's injury with the negative pressure apparatus until sufficient amount of bodily fluid is expressed;

removing the negative pressure apparatus from the site of the sharp's injury;

cleaning the site of the sharp's injury with a cleansing agent; and covering the site of the sharp's injury with a bandage.

15. The method according to claim 14, further comprising the step of using a syringe as the negative pressure apparatus, with the syringe comprising:

a substantially hollow body being closed at one end except for actuating rod aperture, and being open at the opposite end thereof, the open opposite end communicating with an orifice;

a piston being housed within the body, the piston being actuated by a knob located outside of the body, the knob being coupled to the piston via an actuating rod extending through the actuating rod aperture, the actuator rod having a passageway extending axially therealong, and one end of the passageway communicating with an end face of the piston facing the open end and an opposite end of the passageway communicating with an vent located adjacent the knob;

the tip is hollow and defines an intermediate chamber therein, the hollow tip having one end being coupled to the orifice, and the opposite end of the tip defining the inlet which is sufficiently large to encompass the site of the sharp's injury; and a perimeter portion of the inlet of the tip being secured to the flexible perimeter sealing member to facilitate sealing against skin adjacent the site of the sharp's injury for facilitating expressing bodily fluid from the site of the sharp's injury in and through the intermediate reservoir during operation of the apparatus.

16. The method according to claim 15, further comprising the steps of using a kit of parts, for providing first aid to needle stick injury, comprising a container housing the each of the following first aid components:

the tourniquet;

the syringe;

the cleansing agent for cleaning of the site of the sharp's injury; and at lease one bandage for covering the site of the sharp's injury following cleaning.

17. The method according to claim 14, further comprising the steps of applying negative pressure to the site of the sharp's injury, via the negative pressure apparatus, for a time period of at least 5 seconds.

18. The method according to claim 14, further comprising the steps of covering an of the negative pressure apparatus and sending the covered negative pressure apparatus, with the expressed bodily fluid to a test facility for testing of the extracted bodily fluid.

19. An apparatus for generating a negative pressure for expressing bodily fluid from a site of a sharp's injury, the apparatus comprising:

a substantially hollow body being closed at one end except for actuating rod aperture, and being open at the opposite end thereof, the open opposite end communicating with an orifice;

a piston being housed within the body, the piston being actuated by a knob located outside of the body, the knob being coupled to the piston via an actuating rod extending through the actuating rod aperture, the actuator rod having a passageway extending axially therealong, and one end of the passageway communicating with an end face of the piston facing the open end and an opposite end of the passageway communicating with an vent located adjacent the knob;

a hollow tip defining an intermediate chamber therein, the tip having an absorbent material therein to facilitate absorbing and retaining of expressed bodily fluid during use of the apparatus, the hollow tip having one end being coupled to the orifice, and the opposite end of the tip defining an inlet which is sufficiently large to encompass the site of the sharp's injury; and a perimeter portion of the inlet of the tip being provided with a flexible annular sealing member to facilitate sealing against skin adjacent the site of the sharp's injury and expressing bodily fluid from the site of the sharp's injury in and through the intermediate reservoir during utilization of the apparatus, the inlet of the tip being sufficiently large to at least partially receive an end portion of a digit of an individual, the flexible sealing member being permanently supported by a periphery of the inlet and extending radially inwardly from the periphery to a seal against a circumference of the end portion of the received digit; the flexible sealing member having a passage with an inner circumference having a diameter small than a diameter of the inlet to achieve a fluid tight seal with the received digit, and the inner circumference being provided with an annular thickened area to facilitate insertion and removal of the received digit; and the tip being provided with a cap for closing the inlet of the tip, and the cap is connected to the tip by a flexible tether member.

20. An apparatus for generating a negative pressure for expressing bodily fluid from a site of a sharp's injury, the apparatus comprising:

a negative pressure apparatus having a hollow tip for encasing the site of the sharp's injury and generating negative pressure in the tip to facilitate expressing bodily fluid from a site of a sharp's injury; the hollow tip defining an intermediate chamber therein, the hollow tip having one end being coupled to the negative pressure apparatus, and the opposite end of the tip defining an inlet which is sufficiently large to encompass the site of the sharp's injury; and a perimeter portion of the inlet of the tip being provided with a flexible annular sealing member to facilitate sealing against skin adjacent the site of the sharp's injury and expressing bodily fluid from the site of the sharp's injury in and through the intermediate reservoir during utilization of the apparatus, the inlet of the tip being sufficiently large to at least partially receive an end portion of a digit of an individual, and the flexible sealing member extends radially inwardly from a perimeter of the inlet to seal against a circumference of the end portion of the received digit.

* * * * *